United States Patent [19]

Ghajar et al.

[11] Patent Number: 4,970,926
[45] Date of Patent: Nov. 20, 1990

[54] APPARATUS FOR MAKING ANGLED HOLE VENTRICULAR CATHETER

[75] Inventors: Jamshid B. G. Ghajar; Robert J. Hariri; Fathali Ghahremani-Ghadjar, all of New York, N.Y.

[73] Assignee: Neurodynamics, Inc., New York, N.Y.

[21] Appl. No.: 227,397

[22] Filed: Aug. 2, 1988

Related U.S. Application Data

[63] Division of Ser. No. 227,397, Sep. 17, 1987, Pat. No. 4,784,638.

[51] Int. Cl.$^5$ .................... B26D 3/00; B26D 7/01
[52] U.S. Cl. .................... 83/468.94; 83/54; 83/620; 83/638; 83/648; 83/691
[58] Field of Search ............. 83/54, 19, 30, 40, 658, 83/684, 660, 193, 192, 178, 691, 468.93, 468.94, 648, 620, 638; 604/49; 408/115 R

[56] References Cited

U.S. PATENT DOCUMENTS

| | | | |
|---|---|---|---|
| 676,781 | 6/1901 | Stimpson | 83/581 |
| 676,782 | 6/1901 | Stimpson | 83/691 |
| 984,425 | 2/1911 | Gorman | 249/145 |
| 1,544,856 | 7/1925 | Murray | 249/183 |
| 2,116,083 | 5/1938 | Rusch | 83/54 X |
| 3,489,045 | 1/1970 | Ray, Sr. | 83/188 |
| 3,739,461 | 6/1973 | Cupler, II | 29/557 |
| 3,747,450 | 7/1973 | Hudson | 83/30 |
| 3,996,832 | 12/1976 | Schubert et al. | 83/686 |
| 4,149,695 | 4/1979 | Quick et al. | 249/82 |
| 4,181,051 | 1/1980 | Drori | 83/54 X |
| 4,554,849 | 11/1985 | Benham | 83/54 X |
| 4,647,419 | 3/1987 | Helfer et al. | 264/328.9 |
| 4,712,950 | 12/1987 | Reynolds | 408/115 R X |
| 4,750,877 | 6/1988 | McFarlane | 425/573 |

*Primary Examiner*—Hien H. Phan
*Assistant Examiner*—Eugenia A. Jones
*Attorney, Agent, or Firm*—Pennie & Edmonds

[57] ABSTRACT

An apparatus for making a hollow elongated member having a plurality of apertures therein comprising: a first component for supporting a hollow elongated member in a predetermined position and orientation for formation of a plurality of apertures therein; and a second component for forming a plurality of apertures at a predetermined position and orientation and of a predetermined dimension thereof in the hollow elongated member; the second component being guidably received within the first component for alignment therewith. Alternatively, the apparatus includes an insert comprising rod means for forming a plurality of apertures of a predetermined size; and means for forming and supporting the hollow bore of the elongated member. The rod means is positioned at a predetermined orientation with respect to the bore forming means so that the hollow elongated member receives a plurality of apertures therein at a predetermined position, orientation and dimension. This embodiment includes a molding assembly comprising means for forming and supporting a hollow elongated member by substantially completely surrounding the member; a plurality of apertures located in the forming means for guidably receiving the rod means therein to properly orient the insert within a forming means; and means for introducing a polymerizable liquid into the molding assembly so as to form the catheter by polymerization of the liquid therein.

12 Claims, 4 Drawing Sheets

U.S. Patent    Nov. 20, 1990    Sheet 1 of 4    4,970,926
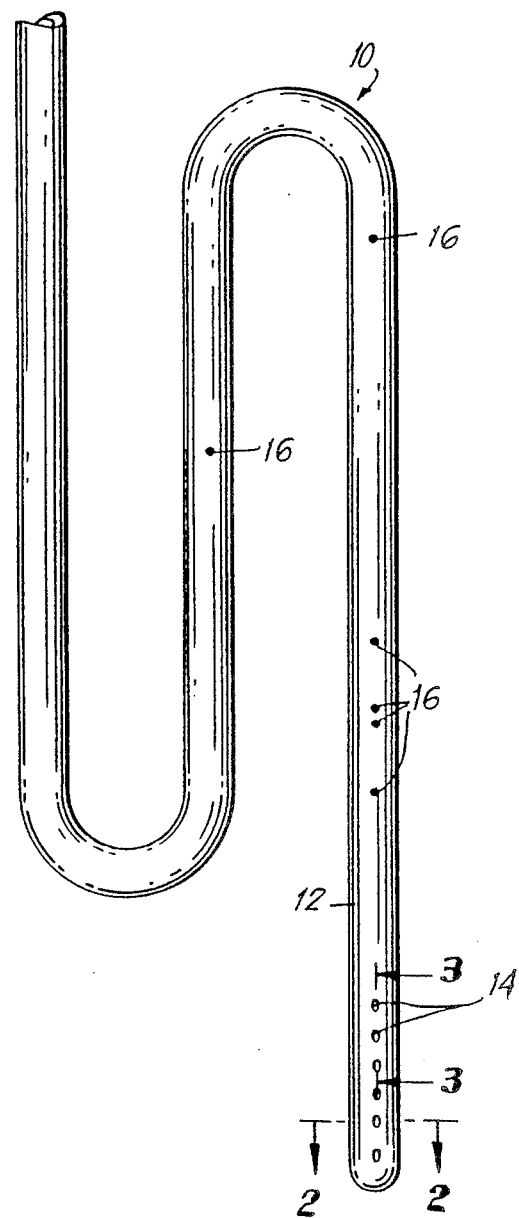
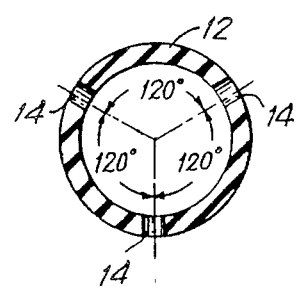
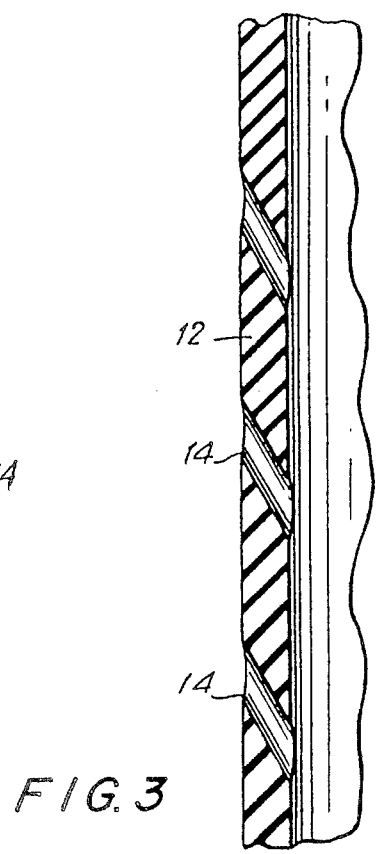

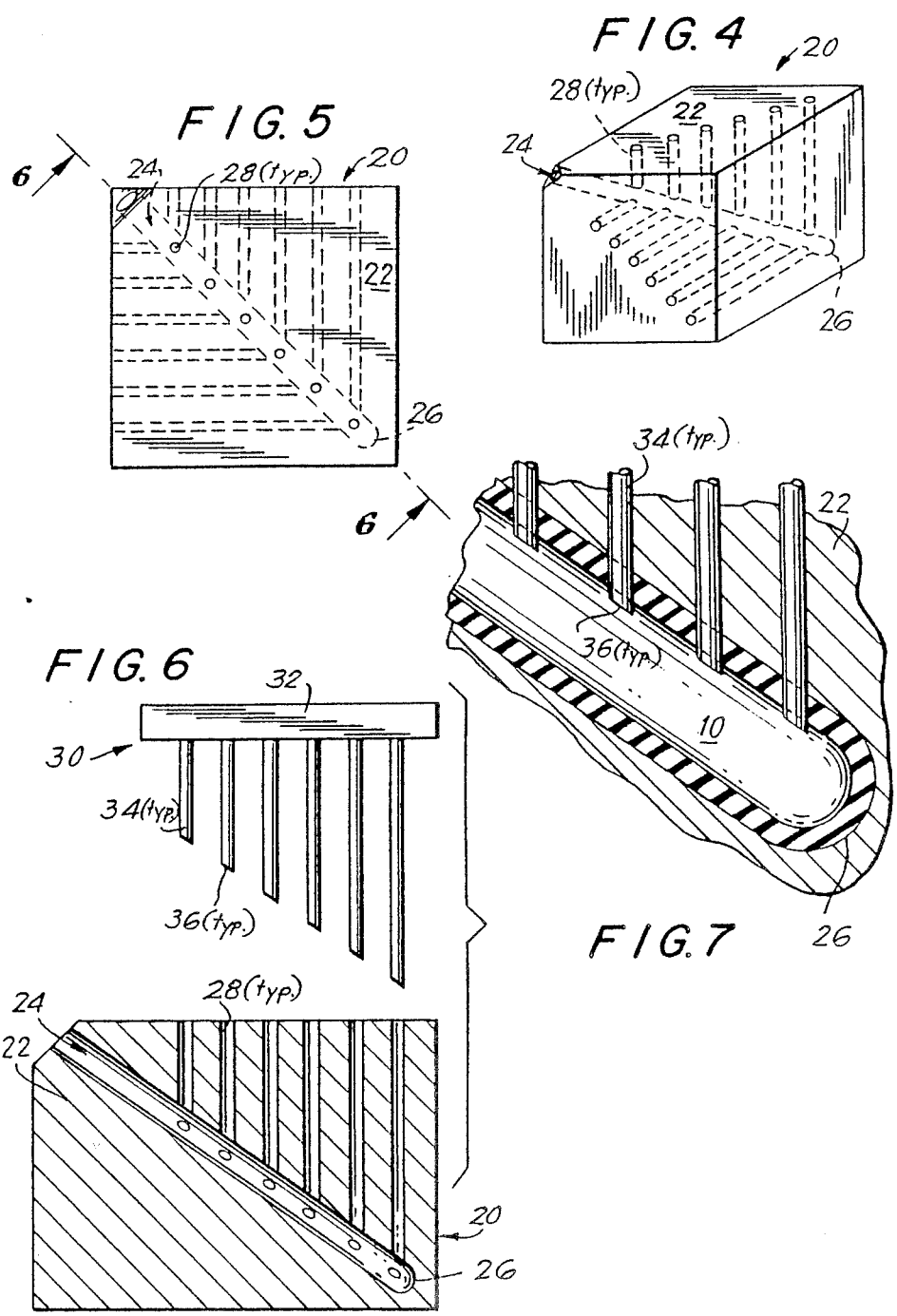

FIG. 8
FIG. 9
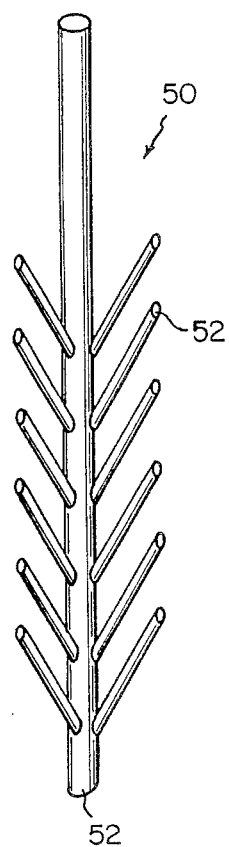
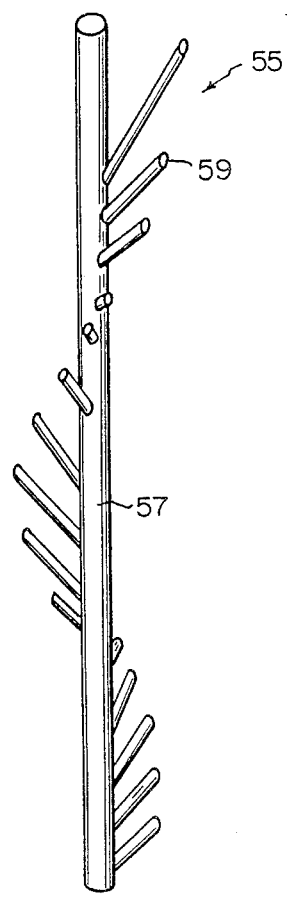

APPARATUS FOR MAKING ANGLED HOLE VENTRICULAR CATHETER

CROSS REFERENCE TO RELATED APPLICATIONS

This is a division and a continuation-in-part of application Ser. No. 098,097, filed Sept. 17, 1987, now U.S. Pat. No. 4,784,638.

TECHNICAL FIELD

The present invention relates to an apparatus for making a ventricular catheter having specifically angled apertures which facilitate access to or drainage of cerebral spinal fluid.

BACKGROUND OF THE INVENTION

The four ventricles of the human brain are interconnected cavities that produce and circulate cerebral spinal fluid (CSF). Procedures involving ventriculostomy, i.e., placement of a catheter into the ventricular system of the brain, form a major part of a neurosurgeon's clinical practice. General areas of application of ventricular catheter placement include intracranial pressure monitoring (ICP), draining or shunting of CSF and the installation of pharmacological therapeutic agents.

CSF drainage is essential for patients with congenital or acquired hydrocephalus. CSF drainage, which can only be performed with an intraventricular catheter, is a life-preserving procedure, because it can immediately reduce intracranial pressure. The ventricular catheter, used to drain CSF, is connected to a peripheral subcutaneous drainage system, i.e., to the peritoneal cavity or systemic circulation via the heart or in the case of ICP to an external drainage collection system. Standard procedures for ventricular catheterization are disclosed in the textbook literature. See, for example, Neurosurgery, edited by Robert H. Wilkins and Setti S. Rengachary, Section A, Chapter 13, Techniques of Ventricular Puncture (McGraw Hill 1984).

The most frequently chosen site for ventricular catheterization is coronal. In most cases, a catheter is inserted in the anterior horn of the lateral ventricle through an orifice or burr hole drilled just anterior to the coronal suture in the midpupillary line of the cranium, i.e., in the frontal bone over the ventricle. The burr hole, only slightly larger than the diameter of the selected catheter to insure a snug fit and provide a seal against CSF leakage, is placed approximately 1 cm anterior to the coronal suture, approximately 10 to 12 cm above the nasion, and approximately 2 to 3 cm from the midline over the nondominant hemisphere. After the burr hole is made, the dura and underlying piaarachnoid are opened and coagulated, for example, with a fine-tipped blade after cauterizing the dural surface.

The lateral ventricles of the human brain form an arc parallel to the arc of the cranium, i.e., the contour of the lateral ventricles parallels the arc of the surface of the skull. Thus, a catheter guided perpendicular to the cranial surface at the point of entry into the cranium will enter the ventricular system. Specifically, any line penetrating a burr hole in the surface of the skull at a 90° angle also bisects the lateral ventricle.

A more recently developed procedure to ensure correct catheter placement is disclosed in U.S. Pat. No. 4,613,324. The apparatus comprises a guide assembly which, when positioned over an orifice drilled in the cranium above the anterior horn of the lateral ventricle, guides a catheter and obturator through the orifice and into the lateral ventricle at an angle normal to an imaginary plane formed by a tangent to the cranium at the orifice, while the corresponding method comprises providing an orifice in the cranium just anterior to a coronal suture in a midpupillary line of the cranium and inserting a ventricular catheter containing an obturator through the orifice towards a lateral ventricle, wherein the catheter containing the obturator is guided through the orifice, by means of a novel guide assembly, at an angle normal to an imaginary plane formed by a tangent to the cranium at the orifice.

A wide variety of catheters are known in the prior art for the purpose of penetrating the ventricular cavity. Such catheters are typically in the form of a hollow tube which is provided with a plurality of apertures at the ventricular or inflow end to permit the passage of CSF from the brain into the catheter and thence to the bloodstream or peritoneal cavity of the patient or to an external drainage system. However, malfunctions frequently occur with such a catheter due to the blockage of the apertures in the inflow end of the catheter. Such blockage is usually caused by the growth of choroid plexus or ependymal tissue within the ventricle into the apertures in the inflow end of the catheter. This tissue may block the apertures in the inflow end of the catheter in a relatively short period of time after the catheter has been inserted into the ventricle thereby rendering the catheter inoperative in relieving excess pressure due to the build-up of CSF within the ventricle. Furthermore, prior art catheter apertures are cut perpendicular to the length of the catheter, thus causing abrasion of brain tissue when the catheter is inserted.

The likelihood of ventricular catheter malfunction by aperture plugging with brain tissue can be lessened by angling the aperture holes in the wall of the catheter such that there is "no see through" flow from the outside to the inside of the lumen. Also, by positioning the rows of apertures 120° apart there is essentially no chance for direct ingrowth of ventricular tissue therethrough. In addition, the apertures are angled away from the direction of the insertion of the catheter into the brain thus lessening the chance of brain abrasion. Further, by slightly stretching the catheter by means of the stylet (which is integral to the catheter and used for placement of it into the brain) the holes will close so that no opening will be visible during the placement thereof, with the holes reopening after the tension on the catheter is relieved by removal of the stylet.

As such, it would be desirable to provide a catheter which overcomes the problems of previously devised ventricular catheters which are emplaceable within a ventricle of a human brain to control the flow of excess fluids to or from the brain. The present invention provides a simple solution which resolves the problems of prior art catheters in a novel and unexpected manner.

SUMMARY OF THE INVENTION

The present invention relates to an apparatus for making catheters having a plurality of angled holes in a flexible, elongated body. Generally, such catheters are hollow elongated members having a plurality of apertures near one end. One embodiment of this apparatus comprises an insert and a molding assembly. The insert includes rod means for forming the plurality of apertures of a predetermined size and shape and means for forming and supporting the bore of the elongated member: the rod means being positioned at a predetermined orientation with respect to the bore forming means so that the hollow elongated member receives a plurality of apertures at a predetermined position, orientation and dimension.

The molding assembly includes means for forming and supporting the hollow elongated member, a plurality of guide holes in the forming means for at least partially receiving the rod means to properly orient the insert therein, and means for allowing a polymerizable liquid to be introduced into the space between the insert and the molding assembly to form the catheter by polymerization therein. Preferably, the rod means and bore forming means of the insert are integral and made of a material which is capable of withstanding temperatures caused by polymerization of the polymerizable liquid.

Generally, the forming and supporting means is constructed in the form of a hollow elongated cylinder having an open end and a closed end wherein the insert is introduced into the open end in a manner such that the rod means extends into a respective guide hole in the cylinder. These rod means and corresponding cylinder holes can be oriented in a spiral configuration around the circumference of the bore forming means or at predetermined stepped intervals along the length of the bore forming means.

The invention also contemplates an apparatus for making a hollow elongated member having a plurality of apertures therein which comprises a cutting assembly having means for cutting a plurality of apertures of a predetermined size, and a holding assembly. The holding assembly includes means for supporting and substantially completely surrounding a portion of a hollow elongated member in the vicinity where apertures are to be made; means adjacent the supporting means for guidably directing the cutting assembly through the supporting means for cutting contact with the hollow elongated member at a predetermined angle thereto; and means operatively associated with the directing and supporting means for positioning the portion of the hollow elongated member at a predetermined orientation with respect to the cutting assembly so that the hollow elongated member can be placed into the holding assembly in a manner to receive a plurality of apertures therein at a predetermined position, orientation and dimension.

The holding assembly preferably comprises a holding block containing an elongated aperture of a size and dimension slightly larger than that of the hollow elongated member so that the member can be easily and removably inserted into the elongated aperture, while the cutting assembly comprises a plurality of elongated rods. The directing means correspondingly comprises a plurality of elongated guide apertures corresponding to the rods of the cutting apparatus but being of slightly greater size and dimension so as to allow the rods to easily and removably pass therethrough for cutting the apertures in the hollow elongated member.

The positioning means includes a stop member for prevention of insertion of an end of the hollow elongated member beyond a predetermined point in the elongated aperture of the holding block, which is advantageously in the shape of a cube with the elongated aperture extending along a diagonal line passing through the center of the cube.

In the most preferred construction, the directing means comprises three sets of elongated apertures, each set being spaced from the others so that the hollow elongated member is provided with rows of apertures spaced 120° apart along its outer periphery. Thus, each of the sets of elongated apertures of the directing means would extend along a diagonal line across a face of the holding block cube to achieve this result.

BRIEF DESCRIPTION OF THE DRAWINGS

Preferred embodiments of the invention are described hereinbelow with reference to the drawing figures wherein:

FIG. 1 is a perspective view of a catheter according to the invention;

FIG. 2 is a cross-sectional view taken along line 2—2 of FIG. 1;

FIG. 3 is a cross-sectional view taken along line 3—3 of FIG. 1;

FIG. 4 is a perspective view of an apparatus for holding the catheter, during the cutting of apertures therein;

FIG. 5 is a top view of the apparatus of FIG. 4;

FIG. 6 is a section taken along lines 6—6 of FIG. 5 over which is shown, an apparatus for cutting apertures in the catheter;

FIG. 7 is an enlarged view of the cutting apparatus piercing the catheter sidewall when the catheter is placed in the holding apparatus of FIG. 4;

FIG. 8 is a perspective view of a symmetric molding insert according to the invention;

FIG. 9 is a perspective view of a spiral molding insert according to, the invention;

DETAILED DESCRIPTION OF THE PREFERRED EMBODIMENTS

Figure 10:
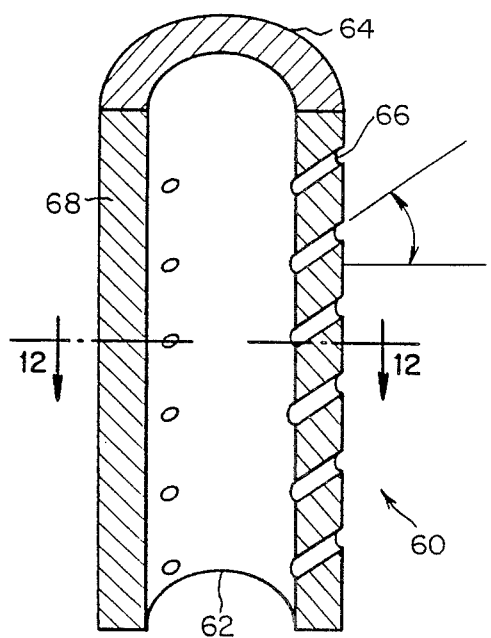
FIG. 10 is a cross sectional view of a mold housing for use with the insert of FIG. 8.

Referring initially to FIG. 1 there is illustrated catheter 10 which is intended for insertion into a ventricle of the human brain for access to or drainage of CSF such as; for example, would be necessary to drain excess CSF during treatment of hydrocephalus. Since the present invention is primarily concerned with the forward or insertion end of the catheter, a detailed description of the opposite or out flow end of the catheter is not provided as such details are well known in the relevant surgical art.

This catheter 10 is a flexible, hollow, elongated member having a sufficient wall thickness for the containment and or transport of fluids therein and therethrough. The forward end 12 of the catheter includes a plurality of apertures 14 for access to CSF in the ventricle of the brain. By "access" what is meant is contact of CSF for removal or drainage from the brain or, conversely, to enable medicaments or other fluids to be directed or delivered into the brain from the catheter through the apertures 14. These apertures 14 are positioned and configured in a predetermined manner so as to allow for a better and more continuous flow of fluids in and through the catheter with less chance of plugging the holes due to ingrowth of a brain tissue when the catheter is placed in the ventricle. Further, the design of the holes enables the catheter placement to be made in an improved, easier manner while causing less abrasion damage to tissue during insertion of the catheter.

As shown in FIGS. 2 and 3, the catheter 10 is designed with 3 sets of holes set 120° apart. These holes are cut at an angle into the wall of the catheter such that the angle of the cut is measured along the longitudinal axis of the catheter in the direction of movement of the catheter when it is inserted into the ventricle. Further, the diameter of each hole in the catheter is proportional to the thickness of the catheter wall so that, as best illustrated in FIG. 3, there is no direct linear visual access to the interior of the catheter when the holes are viewed perpendicular to the longitudinal axis of the catheter.

By preparing the holes in this manner, abrasion of brain tissue is minimized upon insertion of the catheter into the ventricle, so less brain tissue is destroyed as a direct result of such decreased abrasion. Further, by stretching the catheter slightly, the holes in the catheter are closed thus preventing such tissue as may come in contact with the catheter from entering the lumen upon insertion. The stretching of the catheter can easily be accomplished when a rigid placement stylet is used: the body of the catheter being slightly pulled back from the insertion end while the stylet is held, thus allowing the holes to be somewhat flattened. This lack of direct access to the inside of the catheter prevents the growth of brain cells or tissue therein, thus resolving one of the major causes of plugging and malfunction of prior art catheters which utilize 90° or perpendicular apertures. The 120° peripheral offset for each set of holes further minimizes the possibility that choroid plexus or brain cell growth will extend across the inner diameter of the catheter even if such growth does penetrate into one or more of the holes.

Although the holes are advantageously shown as being cut at an angle of 35° with respect to the longitudinal axis of the catheter, it is to be noted that other angles can also be used in this invention provided that direct access to the inside of the catheter is prevented. These other angles would be somewhat dependent upon wall thickness of the catheter, since heavier wall thicknesses would allow a greater range of angles while still preventing direct access into the catheter interior. Suitable angles for any specific catheter construction can be determined from the relationship $d \tan \theta = t$, where d is the diameter of the aperture, t is the wall thickness of the catheter, and $\theta$ is the angle between the cut of the aperture and the longitudinal axis of the catheter body. As shown by the relationship of these variables, the diameter of the aperture must be less than or equal to the wall thickness of the catheter divided by the tangent of the angle. To calculate suitable angles for any particular aperture size and catheter wall thickness, the formula would be $$\theta = \tan^{-1} \frac{t}{d},$$

so that the cosine of the angle, is greater than the quotient of the diameter divided by the thickness.

To assist in the understanding of the invention, direct access is avoided when the diameter of the hole on the outside wall of the catheter does not overlap the diameter of the hole on the inner wall catheter when viewed in a line perpendicular to the wall of the catheter. Thus, it is possible to utilize angles other than 35° although 35° has been found to be particularly advantageous.

By placing the holes to avoid direct access to the inside of the catheter, it is possible to cut the holes larger in diameter than they would be if direct access was provided without weakening the structural integrity of the catheter. These larger holes allow for an increased flow of CSF into the catheter while also making it more difficult for any possible brain cell growth to plug the entire hole, compared to the relatively smaller diameter holes of prior art catheters which provide direct access into the body of the catheter.

The catheter of the invention can be inserted into the ventricle of the brain in any manner currently known, including "freehand" or with the use of a guide. To assist in the proper location and placement of the catheter, a plurality of markings 16 are provided along the length of the catheter body. These markings correspond to predetermined insertion lengths of the catheter and enables the surgeon to know precisely how far the tip of catheter is inserted into the ventricle. By making these markings of a radioopaque material such as barium, the depth of placement of the catheter can easily be monitored by conventional techniques. Furthermore, if desired, the forward section of the catheter in the area around the apertures can also be made of a radioopaque material for viewing on various scanning equipment the precise placement of the forward end and tip of the catheter.

The improvements provided by the catheter of this invention are significant in that the physician does not require any guess work to determine the precise placement of the catheter in the patient's brain. Furthermore, when so placed, the catheter provides improved fluid delivery and/or removal with minimal disturbance of the surrounding brain cells while also discouraging brain tissue growth into the catheter apertures. As mentioned above, the catheter can be inserted in the brain in any manner commonly utilized. Rather than a "free hand" technique, it is advantageous to utilize a guide assembly to insure correct catheter placement.

A preferred guide apparatus and method of insertion of a catheter into the ventricle is disclosed in U.S. Pat. No. 4,613,324, the disclosure of which is expressly incorporated herein by reference thereto. As shown in the patent, a stylet is used to assist in the insertion of the catheter. As noted above, the stylet can be used to stretch the present catheters so that the angled apertures can be flattened to minimize the abrasion of brain tissue during insertion. Also, this flattening operation slightly reduces the overall diameter of the catheter which further reduces such abrasion.

It is known for certain applications to utilize a second stylet for guiding the catheter into the ventricle. In prior art catheters, this second stylet is inserted into one of the apertures at the forward end of the catheter. Since those apertures are cut at 90°, an unwieldy assembly is created. Any attempt to align the second stylet parallel to and adjacent the first stylet and catheter causes the tip to be somewhat bent, thus causing further difficulties in its insertion and penetration of the ventricle. The present invention significantly reduces and minimizes this problem since the angled holes are more receptive to the introduction of the second stylet in a compact orientation (i.e., in a "V" shape, rather than an "L" shape) which greatly enhances the manipulation of the catheter and stylets during placement in the ventricle.

The catheters of the invention can be easily manufactured in a highly accurate and reproducible manner by utilizing the apparatus of the invention. In one embodiment, the apparatus includes a holding block with rod-like cutting elements, while an alternate embodiment relates to an apparatus for molding these catheters in the desired shape, form and configuration.

FIGS. 4 and 5 illustrate a holding apparatus 20 in the form of a machined metal block or cube 22. A longitudinal extending aperture 24 extends diagonally from one corner of the cube through the center to the opposite corner. The closed end 26 of the aperture 24 is within the confines of the cube and serves as a positioning means or stop member for the hollow elongated member. The diameter of the aperture 24 is only slightly greater than the diameter of the catheter 10 so that the catheter is fully supported in the aperture when the angled holes are made in the catheter wall.

FIG. 6 illustrates a cutting apparatus 30 consisting of a handle 32 and a plurality of hollow tube cutting elements 34 each of which have a sharpened tip 36. The tube elements 34 extend through guide apertures 28 on one face of the cube 22 until contact is made with the catheter 10. As best illustrated in FIG. 7, the cutting tubes 34 penetrate the catheter wall, thus forming the appropriately sized holes therein at the predetermined angle, position and configuration.

Prior art catheters, as noted above, have four sets of holes oriented 90° apart along the circumference of the catheter. In addition to weakening the strength and structural integrity of the catheter in the tip area, holes on opposite sides of the catheter (i.e., those 180° apart) are made simultaneously by a punching tool. This results in holes on one side being larger in diameter than those on the opposite side. Therefore, two sets of holes are large and two are small. This non-uniformity affects CSF flow and the smaller holes can easily become blocked by brain tissue growth, thus causing reduced operation of those catheters.

The present invention resolves these problems by accurately and precisely placing three sets of uniform holes cut at the desired angle to the catheter body and spaced apart exactly by 120°. This results in increased flow through the holes, higher strength and integrity of the catheter body, and greater ease of insertion and placement of the catheter in the ventricle.

FIGS. 4 through 6 illustrate the placement of guide apertures 28 on the various faces of the cube. In a most preferred arrangement, these guides are positioned in a diagonal line along the top and two side faces of the cube 22, so that each set of holes is placed 120° apart around the periphery or circumference of the catheter body. As noted previously, it is highly advantageous to make the holes in the catheter 10 at an angle of 35° with respect to the longitudinal axis of the catheter.

This apparatus guarantees the accuracy of the hole cutting at the appropriate angle as well as the precise spacing of the holes relative to each other around the periphery or circumference of the catheter. To cut the holes, the user merely inserts the tubes 34 of cutting apparatus 30 into the guides 28 when a catheter is placed in the holding block 20. The cutting apparatus 30 after piercing the catheter wall 10 is then removed, resulting in placement of the holes at the precise orientation and configuration in a simple manner which allows for repeatable and rapid production of such angled hole catheters. Further, the precision obtained in utilizing this apparatus is very high and reproducible to facilitate mass production.

Figure 11:
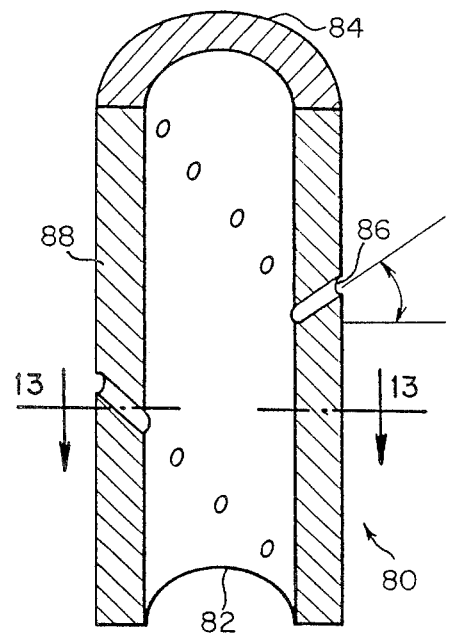
FIG. 11 is a cross sectional view of a mold housing for use with the insert of FIG. 9.
Figure 13:
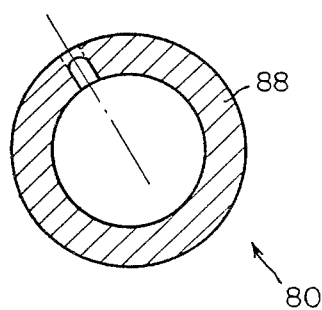
FIG. 13 is a cross sectional view of the mold of FIG. 11 taken along lines 13—13 thereof.
Figure 12:
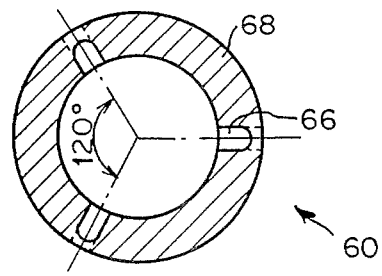
FIG. 12 is a cross sectional view of the mold of FIG. 10 taken along lines 12—12 thereof.

The preceding apparatus has been found to be suitable for constructing apertured catheters of a variety of materials for particular applications. When very small diameter holes in thin-walled silicone catheters are desired, the quality of side-wall smoothness necessary to prevent cells or tissue from binding and plugging the catheter holes is difficult to obtain by the use of the cutting apparatus. Accordingly, applicants have devised a molding system which achieves all the desired results. This embodiment illustrated in FIGS. 8 through 13, is discussed below. Generally, a disposable insert is placed in a molding assembly prior to the injection of the polymerizable silicone material. This insert is retained in place until the silicone material cures. Thereafter, the insert and catheter are removed from the mold and the insert is discarded. This technique enables the user to produce extremely smooth, very small, angled holes at any orientation, position or configuration in a relatively simple and highly reproducible manner.

FIGS. 8 and 9 illustrate two preferred disposable inserts 50, 55. Each of these inserts has an elongated body portion 52, 57 and a plurality of rod like extensions 52, 59 extending from the body at a predetermined angle. As mentioned above, it is highly advantageous to make the holes of the catheter at an angle of 35 degrees with respect to its longitudinal axis. Thus, the rod-like extensions 52, 59, of these inserts are positioned at an angle preferably of 35 degrees with respect to the axis of the body member 52, 57. FIG. 8 illustrates an insert for forming three rows of apertures in the catheter, while FIG. 9 illustrates a spiral orientation of such apertures about the circumference of the catheter body.

FIGS. 10 through 13 illustrate the molding cylinders 60, 80 for use with the previously described inserts 50, 55. Each mold includes an open end 62, 82 which enables insertion of the corresponding inserts 50, 55, and a closed end 64, 84 which is used to form the insertion tip of the catheter. These molds 60, 80 include a plurality of guide apertures 66, 86 for at least partially receiving the rod like members 52, 59 of the respective inserts 50, 55. The guide holes 66, 86 extend through the wall 68, 88 of the molding cylinders 60, 80 at an angle which corresponds to the desired angle of the catheter holes.

In manufacturing, a plurality of molds 60, 80 and a much greater number of inserts 50, 55 are prepared. Since the molds 60, 80 are reusable, basically any material can be used which would provide a useful service life. This would include, for example, steel, stainless steel, aluminum, etc. and certain engineering thermoplastics may also be suitable. These materials must be sufficiently strong to retain the insert and withstand the temperatures anticipated for the polymerization of the material used to form the catheter. Such mold material must also be dimensionally stable over the entire curing temperature range.

The insert 50, 55 should be made of a selflubricating material that does not bind or stick to the polymerizable liquid used to form the catheter. Also, the self-lubricating material must be sufficiently flexible so that it can be easily inserted and drawn out of the mold without damaging the catheter. At this time, the most preferred material for the insert is an injection molded polyamide material.

A preferred material for the catheter itself, is a polymerizable silicon liquid which has a very low injection and curing temperature, i.e., about 100° F. While this requires a relatively long curing time, high production rates can be achieved through the use of multiple molding cavities. The inserts are disposable so that each insert can only be used to make one catheter. As noted above, the mold itself can be reused an infinite number of times.

During manufacturing, after the insert is placed within the mold, and the rod member properly positioned within the guide holes of the mold, the polymerizable liquid is introduced into the space between the insert and the mold. The liquid is then allowed to polymerize and cure to form the catheter. The insert and catheter are removed from the mold and the insert is then destroyed to form the final catheter product.

The preceding molding technique provides numerous advantages, including:

(1) the catheter holes can be configured in any shape or size relative to the axis of the catheter. For example, spiral, off-set 90 degree or off-set 120 degree holes can easily be obtained.

(2) the angle of the hole relative to the axis of the catheter can be easily changed by providing different mold inserts and mold cavities. This allows optimization of the hole angle compared to the hole diameter as a function of cell growth. This relationship is governed by the formula given above.

(3) this apparatus assures that no "flashing" will occur on the internal bores of the catheter. Any excess material due to "flashing", will be visible on the exterior surface of the catheter and can be easily trimmed therefrom.

(4) this apparatus assures that each catheter can be manufactured to very close tolerances with little or no variation in the construction of each device: hence, a high degree of reproducibility in mass production is achieved.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. An apparatus for making a hollow elongated member having a plurality of apertures therein, comprising:
a cutting assembly comprising means for cutting a plurality of apertures of a predetermined size in said hollow elongated member; and
a holding assembly comprising:
a machined metal cube containing an elongated aperture of a size and dimension slightly larger than that of said hollow elongated member so that said elongated member can be easily and removably inserted into said elongated aperture, said elongated aperture extending along a diagonal line passing through the center of said cube;
means in said cube for guidably directing said cutting assembly through said cube for cutting contact with said hollow elongated member at a predetermined angle thereto; and
means operatively associated with said cube and said directing means for positioning said portion of said hollow elongated member at a predetermined orientation with respect to said cutting assembly so that said hollow elongated member can be placed into said holding assembly in a manner to receive a plurality of said apertures therein at a predetermined position, orientation and dimension.

2. The apparatus of claim 1 wherein said directing means comprises at least three sets of alignment apertures, each set being spaced from the others so that said hollow elongated member will be provided with three rows of apertures spaced about 120° apart along its outer periphery.

3. The apparatus of claim 2 wherein the cutting means includes a plurality of elongated tubes.

4. The apparatus of claim 2 wherein the cutting means includes a plurality of rod members.

5. The apparatus of claim 3 wherein said alignment apertures are of slightly greater size and dimension than said elongated tubes so as to allow said tubes to easily and removably pass therethrough for cutting said plurality of apertures in said hollow elongated member.

6. The apparatus of claims 3 or 4 wherein said cutting means have a cutting end and are connected by an alignment member at their ends opposite said cutting end.

7. The apparatus of claim 6 wherein said alignment member contacts said cube so that the cutting ends do not pass the longitudinal axis of said hollow elongated member.

8. The apparatus of claim 4 wherein said alignment apertures are of slightly greater size and dimension than said rod members so as to allow said rod members to easily and removably pass therethrough for cutting said plurality of apertures in said hollow elongated member.

9. The apparatus of claim 2 wherein each of said sets of alignment apertures of the directing means extends along the diagonal line across a face of the metal cube.

10. The apparatus of claim 1 wherein said positioning means comprises a stop member for prevention of insertion of an end of said hollow elongated member beyond a predetermined point in said elongated aperture of said metal cube.

11. The apparatus of claim 1 wherein said elongated aperture extends only partially through said cube.

12. The apparatus of claim 1, wherein said directing means is positioned so that said apertures are formed at an angle with respect to the axis of said elongated member such that, when said apertures are viewed perpendicular to the longitudinal axis of said hollow elongated member, there is no direct linear access to the interior of said hollow elongated member.

* * * * *